(12) United States Patent
Kogoshi et al.

(10) Patent No.: US 10,625,007 B2
(45) Date of Patent: Apr. 21, 2020

(54) BLOOD PURIFICATION APPARATUS AND BLOOD PURIFICATION SYSTEM

(71) Applicant: Nikkiso Company Limited, Tokyo (JP)

(72) Inventors: Kentaro Kogoshi, Shizuoka (JP);
Masahiro Aoshima, Shizuoka (JP);
Satoshi Takeuchi, Shizuoka (JP)

(73) Assignee: Nikkiso Company Limited, Tokyo (JP)

( * ) Notice: Subject to any disclaimer, the term of this patent is extended or adjusted under 35 U.S.C. 154(b) by 30 days.

(21) Appl. No.: 15/850,820

(22) Filed: Dec. 21, 2017

(65) Prior Publication Data

US 2018/0110911 A1  Apr. 26, 2018

Related U.S. Application Data

(63) Continuation of application No. PCT/JP2016/068787, filed on Jun. 24, 2016.

(30) Foreign Application Priority Data

Jun. 24, 2015 (JP) ................................ 2015-126901

(51) Int. Cl.
*A61M 1/16* (2006.01)
*A61M 1/10* (2006.01)
(Continued)

(52) U.S. Cl.
CPC ........ *A61M 1/1601* (2014.02); *A61M 1/1006* (2014.02); *A61M 1/168* (2013.01);
(Continued)

(58) Field of Classification Search
None
See application file for complete search history.

(56) References Cited

U.S. PATENT DOCUMENTS 418,565 A  12/1889  St. John
5,441,636 A  8/1995  Chevallet et al.
(Continued)

FOREIGN PATENT DOCUMENTS

EP  2005982 A1  12/2008
EP  2163271 A1  3/2010
(Continued)

OTHER PUBLICATIONS

International Search Report from the Japanese Patent Office for Application No. PCT/JP2016/068787, dated Sep. 27, 2016.
(Continued)

*Primary Examiner* — Richard C Gurtowski
(74) *Attorney, Agent, or Firm* — Young Basile Hanlon & MacFarlane, P.C.

(57) ABSTRACT

A blood purification apparatus and a blood purification system that is operable with increased ease even if a blood purifier requires special treatment conditions and operational settings is used. A blood purification apparatus includes a blood purifier for giving blood purification treatment by purifying blood of a patient; and a control device that executes, in accordance with preset treatment conditions and/or operational settings, an operation for performing the blood purification treatment or an operation associated with the blood purification treatment. The blood purification apparatus includes a registering device that is capable of registering, in advance, the treatment conditions and/or operational settings corresponding to a performance, characteristic, or function of the blood purifier; and a changing device that is capable of changing the treatment conditions and/or operational settings to the treatment conditions and/or operational settings registered by the registering device, in accordance with the blood purifier to be used in the blood purification treatment.

20 Claims, 14 Drawing Sheets

(51) Int. Cl.
*A61M 1/36* (2006.01)
*A61M 1/34* (2006.01)

(52) U.S. Cl.
CPC ........ *A61M 1/3607* (2014.02); *A61M 1/3643* (2013.01); *A61M 1/342* (2013.01); *A61M 2205/3379* (2013.01); *A61M 2205/3561* (2013.01); *A61M 2205/502* (2013.01)

(56) References Cited

U.S. PATENT DOCUMENTS

| | | | |
|---|---|---|---|
| 6,044,691 | A | 4/2000 | Kenley et al. |
| 7,488,301 | B2 | 2/2009 | Beden et al. |
| 8,991,414 | B2 | 3/2015 | Gronau et al. |
| 2002/0104800 | A1* | 8/2002 | Collins ................ A61M 1/342 210/646 |
| 2004/0204634 | A1 | 10/2004 | Womble et al. |
| 2006/0079826 | A1 | 4/2006 | Beden et al. |
| 2009/0024070 | A1 | 1/2009 | Gelfand et al. |
| 2009/0101566 | A1 | 4/2009 | Crnkovich et al. |
| 2009/0222119 | A1* | 9/2009 | Plahey .................... A61M 1/16 700/94 |
| 2010/0168640 | A1 | 7/2010 | Kopperschmidt et al. |
| 2010/0274168 | A1 | 10/2010 | Gronau et al. |
| 2010/0274172 | A1 | 10/2010 | Guenther et al. |
| 2011/0017665 | A1* | 1/2011 | Updyke ............. A61M 1/1696 210/638 |
| 2011/0139690 | A1 | 6/2011 | Akita et al. |
| 2012/0000547 | A1 | 1/2012 | Gronau et al. |
| 2012/0123322 | A1 | 5/2012 | Scarpaci et al. |
| 2013/0020237 | A1 | 1/2013 | Wilt |
| 2013/0035626 | A1 | 2/2013 | Suzuki |
| 2013/0133036 | A1 | 5/2013 | Wang et al. |
| 2015/0021244 | A1 | 1/2015 | Furuhashi et al. |
| 2016/0175508 | A1 | 6/2016 | Murakami et al. |

FOREIGN PATENT DOCUMENTS

| | | |
|---|---|---|
| EP | 2292284 A1 | 3/2011 |
| EP | 2716308 A1 | 4/2014 |
| JP | S60-153138 | 10/1985 |
| JP | S62-070529 U1 | 5/1987 |
| JP | S63-106445 U1 | 7/1988 |
| JP | H06-205827 A | 7/1994 |
| JP | H06-292722 A | 10/1994 |
| JP | 2002-095741 A | 4/2002 |
| JP | 2003-010319 A | 1/2003 |
| JP | 2004-016619 A | 1/2004 |
| JP | 2010-273693 A | 9/2005 |
| JP | 2005-253555 A | 4/2006 |
| JP | 2006-280775 A | 10/2006 |
| JP | 2006-314458 A | 11/2006 |
| JP | 2007-000238 A | 1/2007 |
| JP | 2007-007435 A | 1/2007 |
| JP | 2007-167108 A | 7/2007 |
| JP | 2007-282737 A | 6/2008 |
| JP | 2009-112651 A | 5/2009 |
| JP | 2010-000161 A | 5/2009 |
| JP | 2009-131412 A | 6/2009 |
| JP | 2010-273784 A | 12/2009 |
| JP | 2010-269050 A | 12/2010 |
| JP | 2010-538803 A | 12/2010 |
| JP | 2011-120821 A | 6/2011 |
| JP | 2011-120822 A | 6/2011 |
| JP | 2011-120823 A | 6/2011 |
| JP | 2012-000291 A | 1/2012 |
| JP | 2012-139405 A | 7/2012 |
| JP | 2012-200275 A | 10/2012 |
| JP | 2012-524563 A | 10/2012 |
| JP | 2013-533793 A | 8/2013 |
| JP | 2014-000307 A | 1/2014 |
| JP | 2014-004194 A | 1/2014 |
| JP | 2014-070335 A | 4/2014 |
| JP | 2014-217528 A | 11/2014 |
| JP | 2014217528 A | 11/2014 |
| WO | 1999/62574 A1 | 12/1999 |
| WO | 2005/118485 A | 12/2005 |
| WO | 2009/081196 A1 | 7/2009 |
| WO | 2011/099521 A1 | 5/2011 |
| WO | 2011/132123 A1 | 10/2011 |

OTHER PUBLICATIONS

Co-Pending U.S. Appl. No. 14/497,369, filed Sep. 26, 2014, published as US 2015/0021244 on Jan. 22, 2015.
Co-Pending U.S. Appl. No. 14/615,839, filed Feb. 6, 2015, published as US 2015/0151036 on Jun. 4, 2015.
Co-Pending U.S. Appl. No. 15/055,216, filed Feb. 26, 2016, published as US 2016/0175508 on Jun. 23, 2016.
Co-Pending U.S. Appl. No. 15/343,699, filed Nov. 4, 2016.
Co-Pending U.S. Appl. No. 15/631,332, filed Jun. 23, 2017.
Extended European Search Report dated Jan. 23, 2019, Application No. 16814475.6.

* cited by examiner

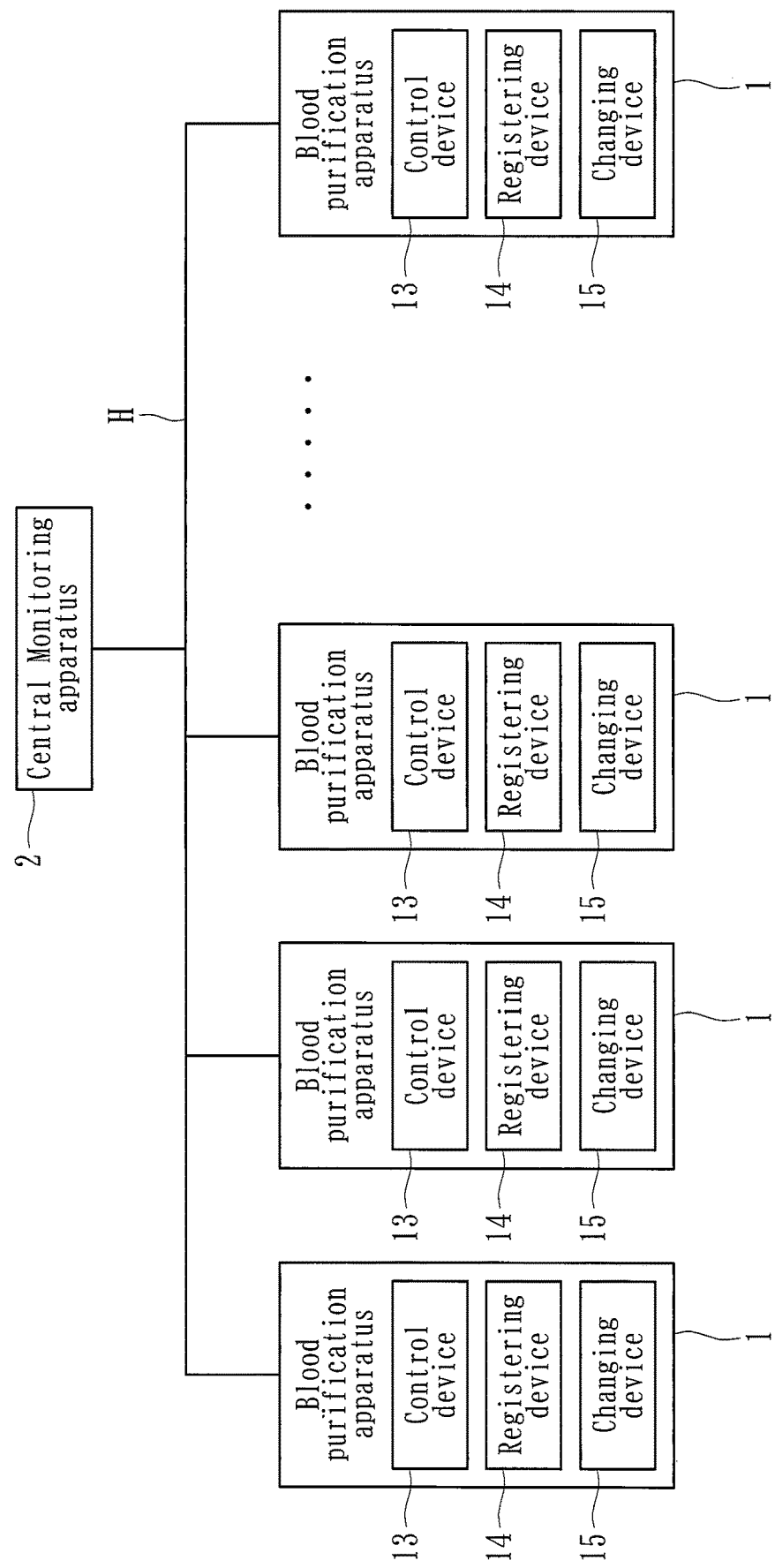

[Fig. 2]
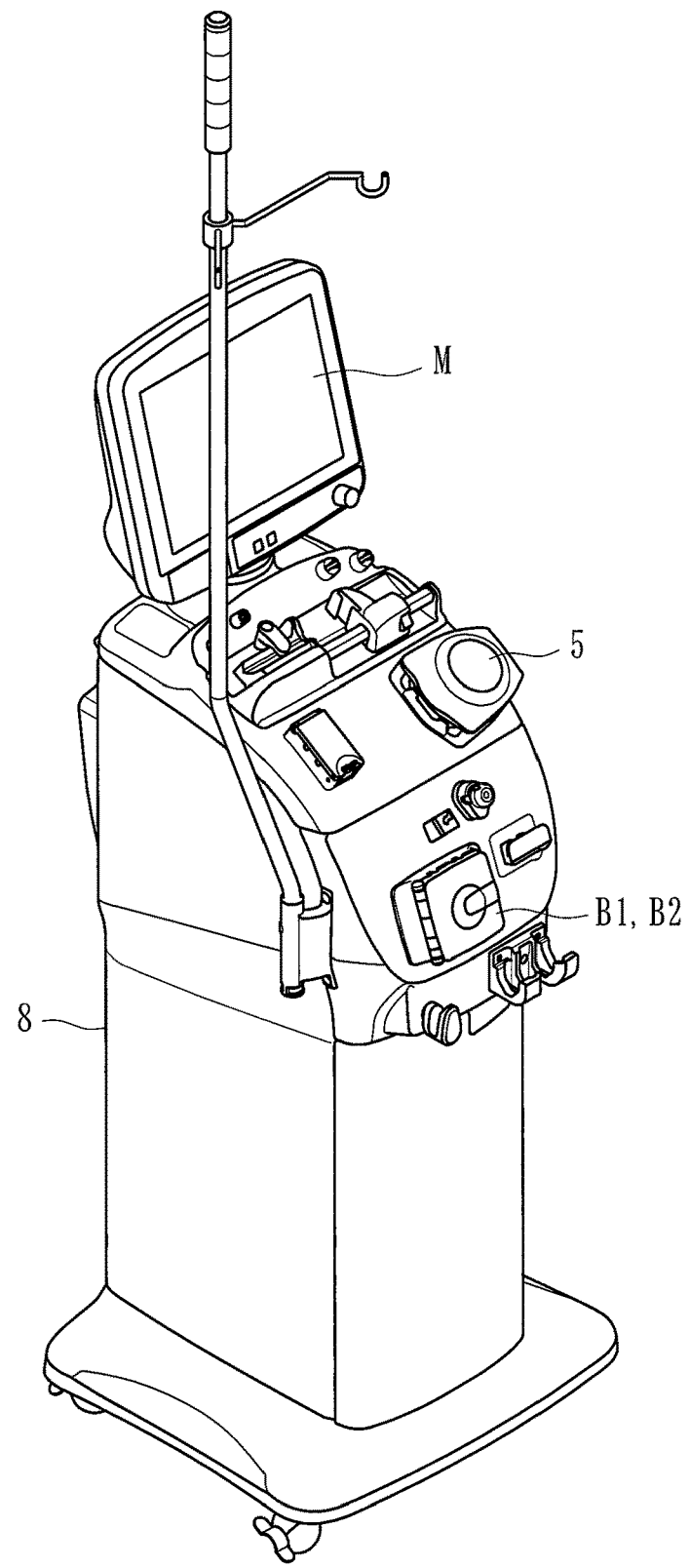

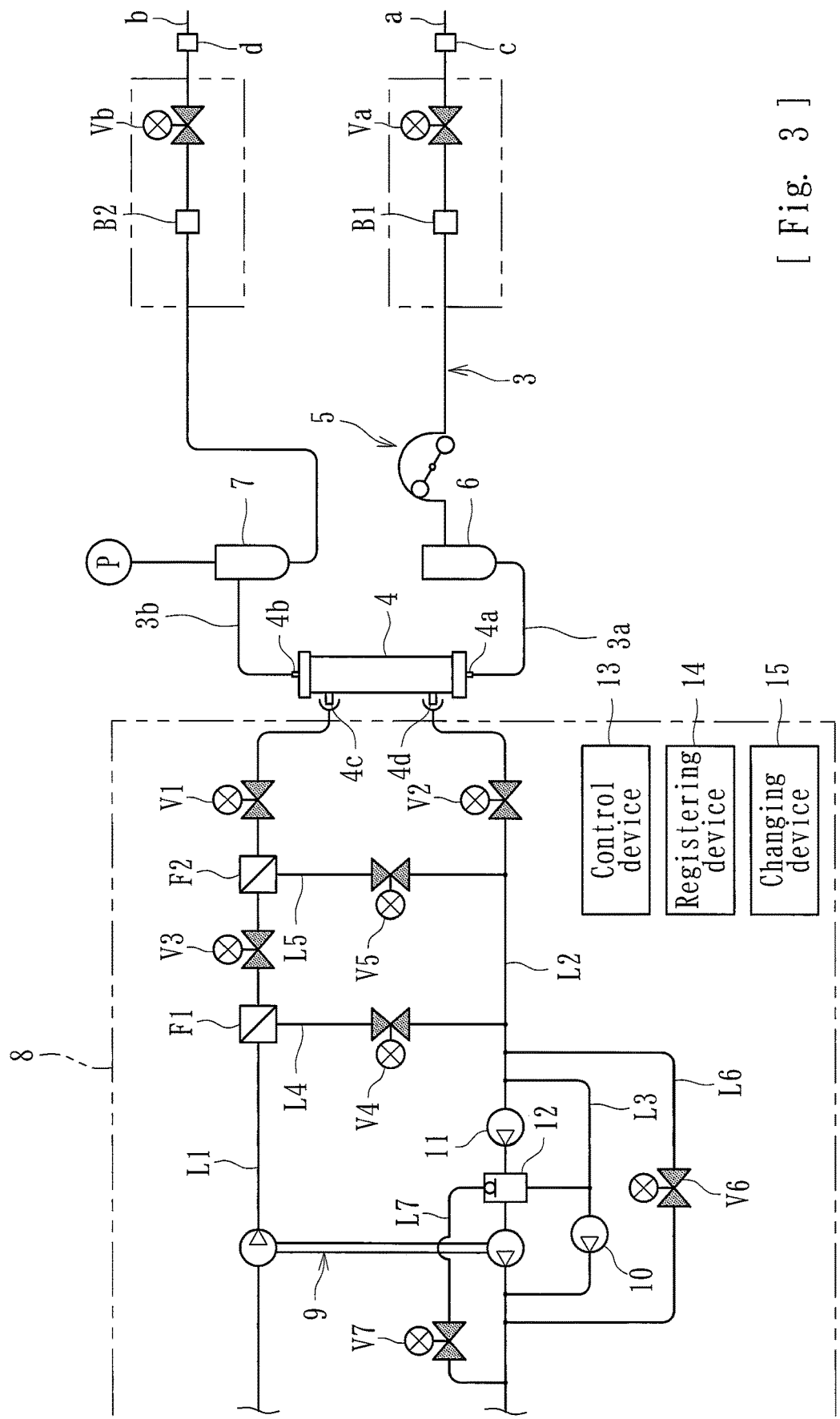
[ Fig. 3 ]

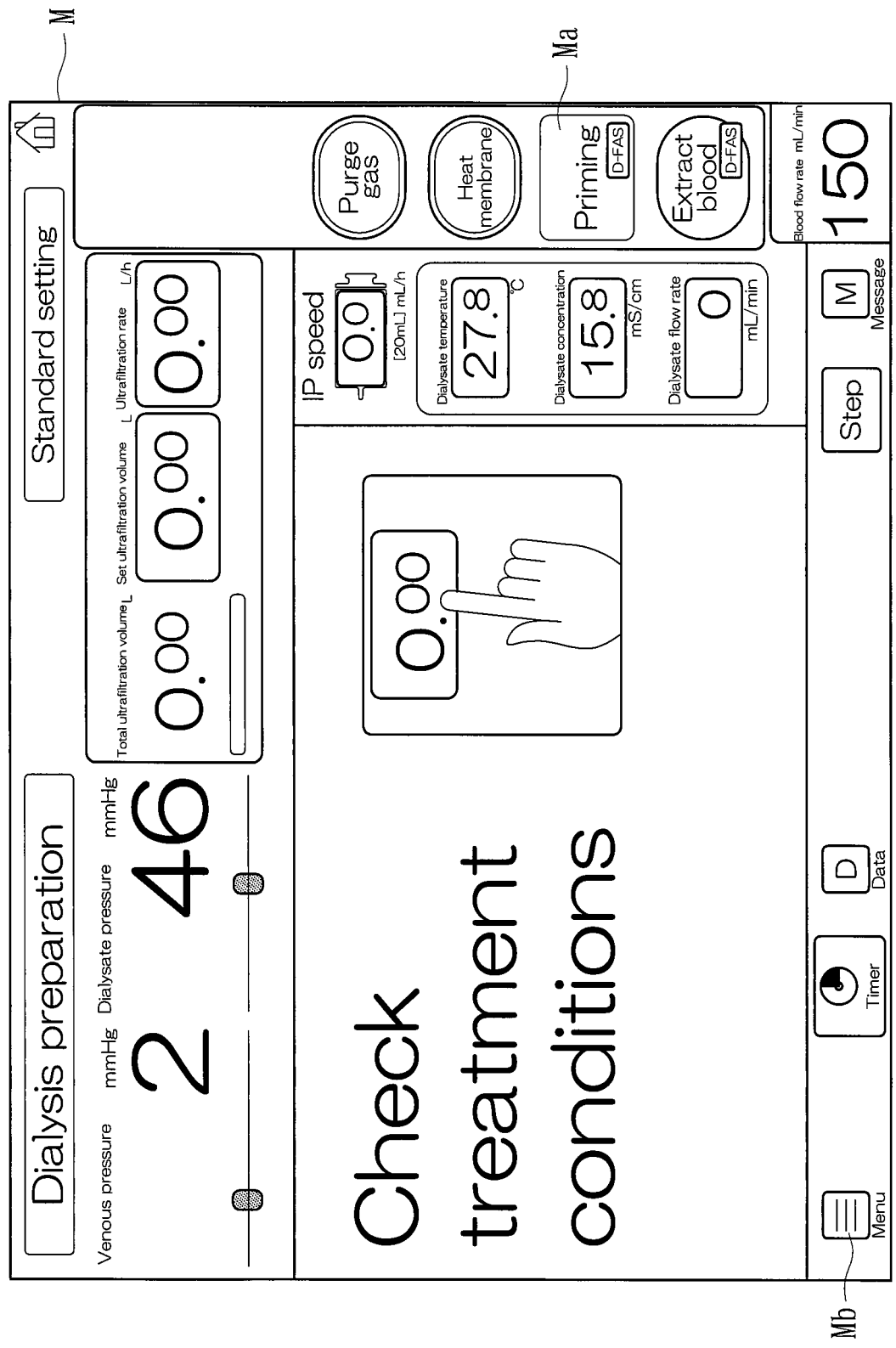
[ Fig. 4 ]

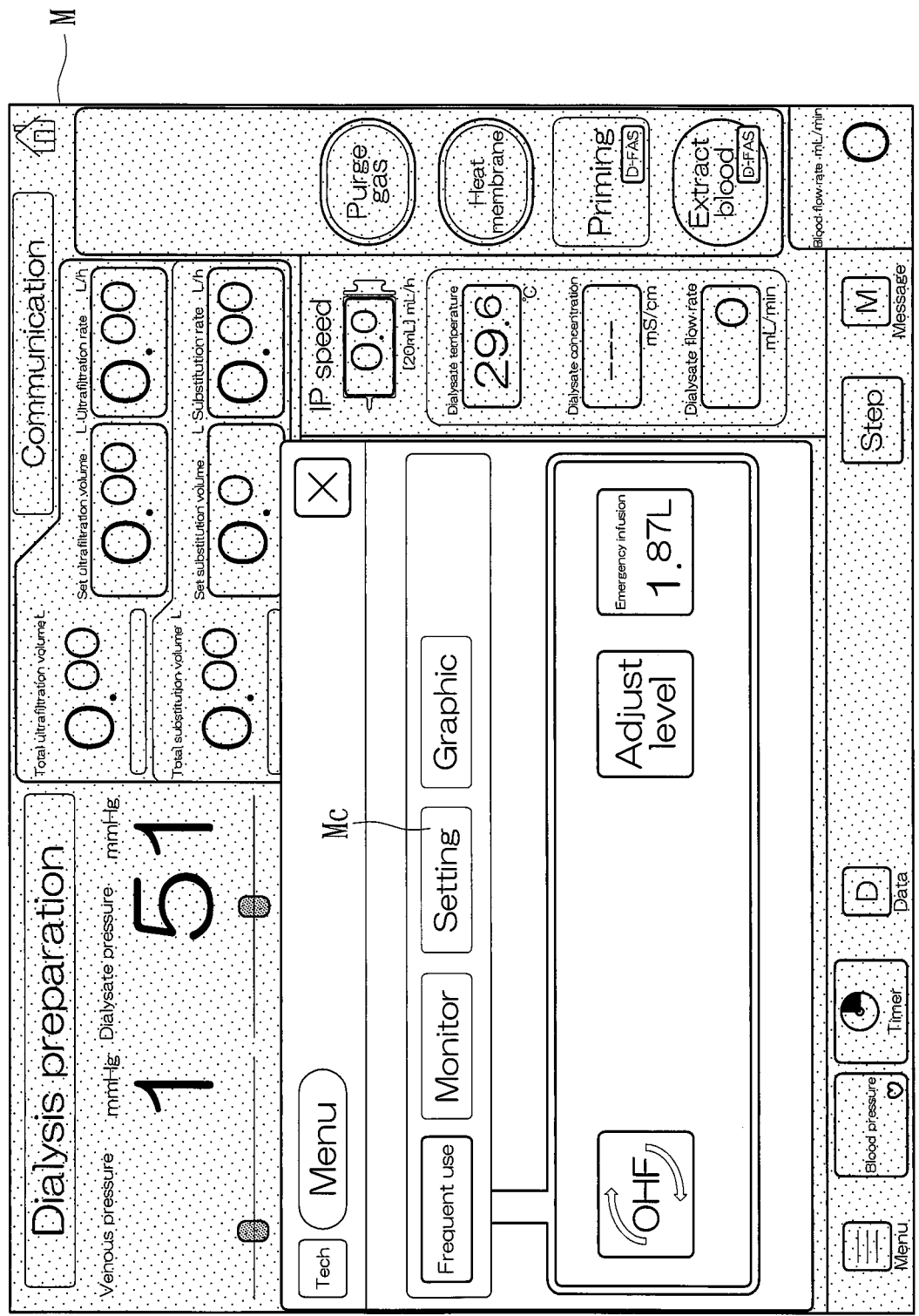
[Fig. 5]

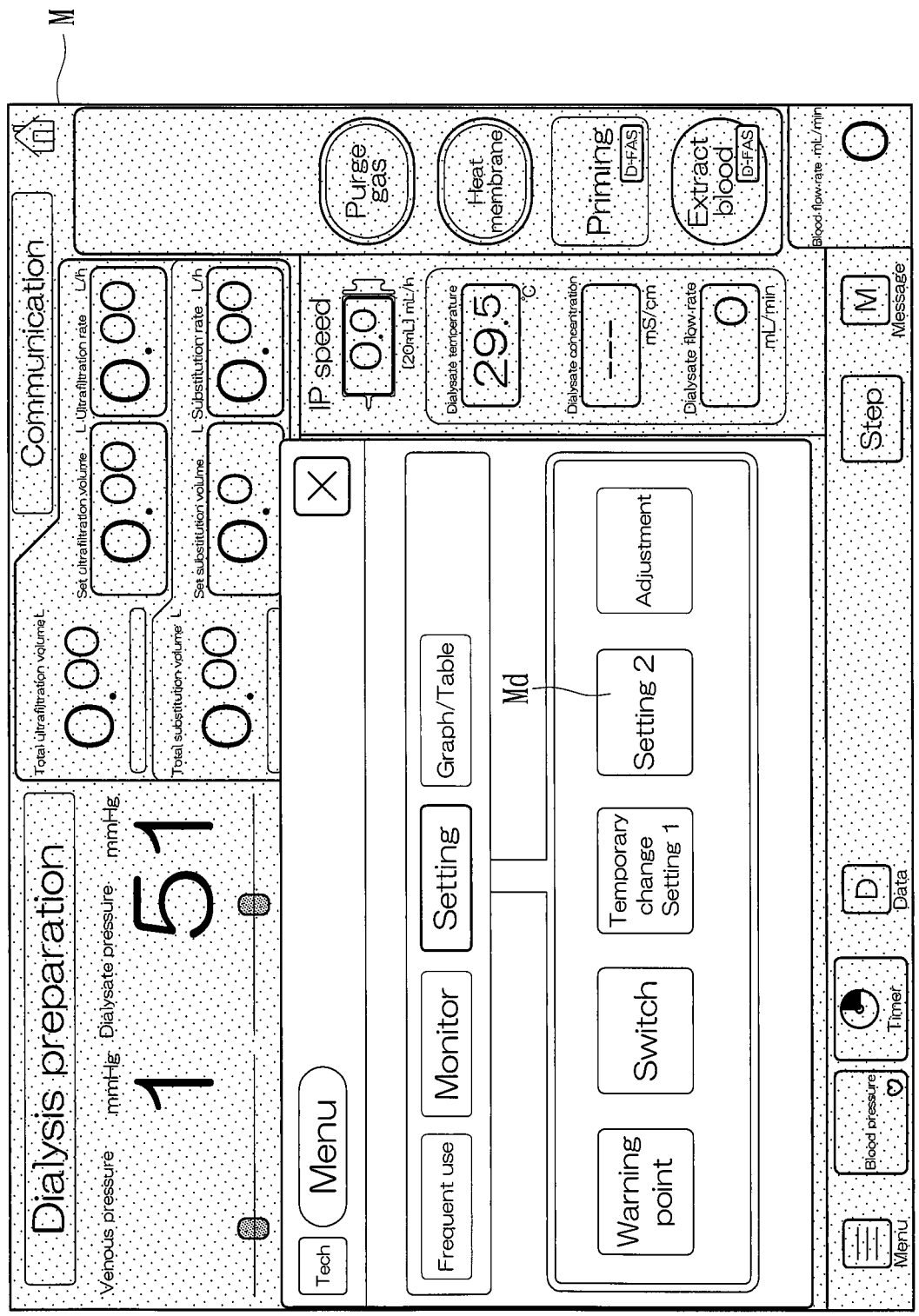
[Fig. 6]

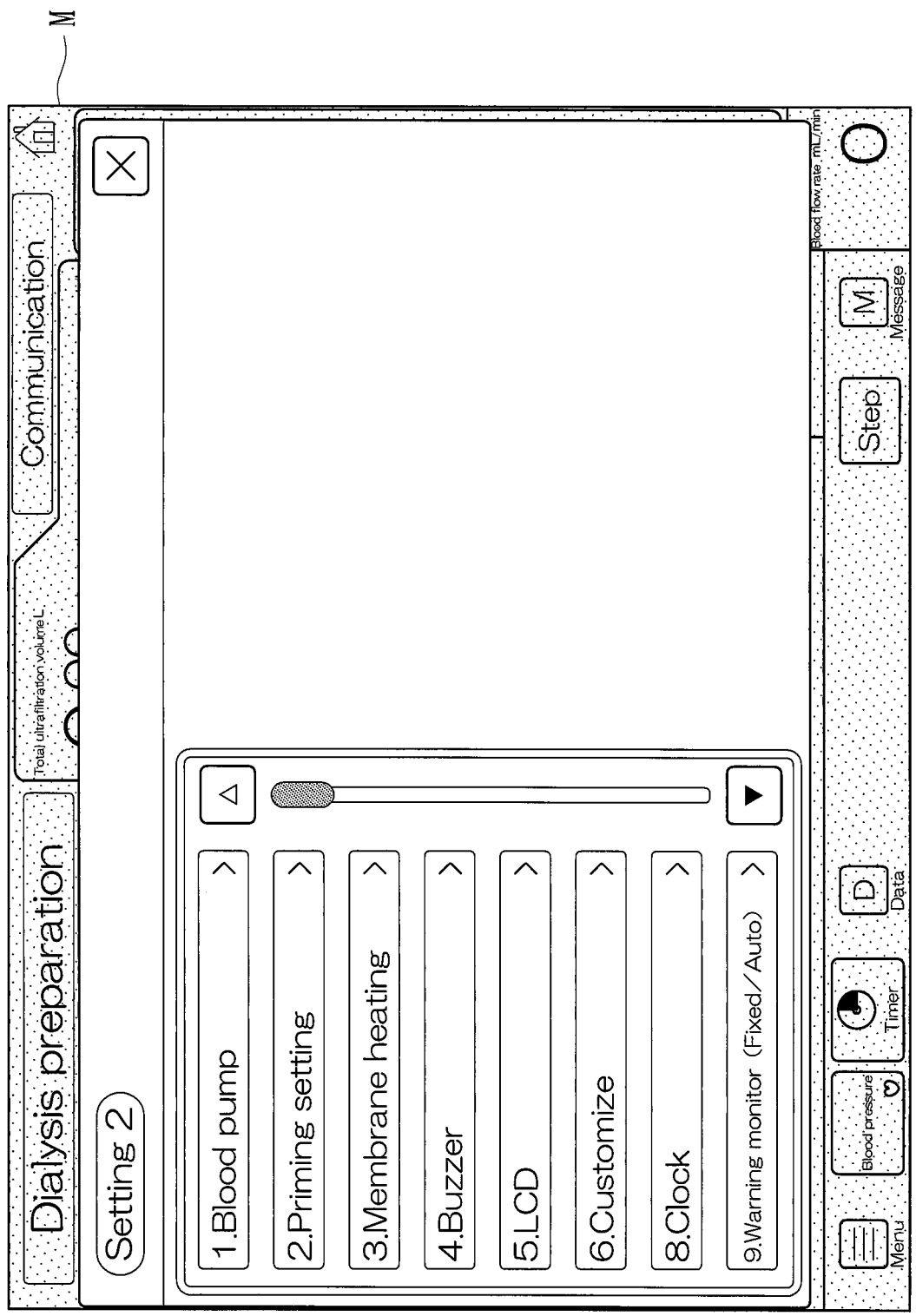
[Fig. 7]

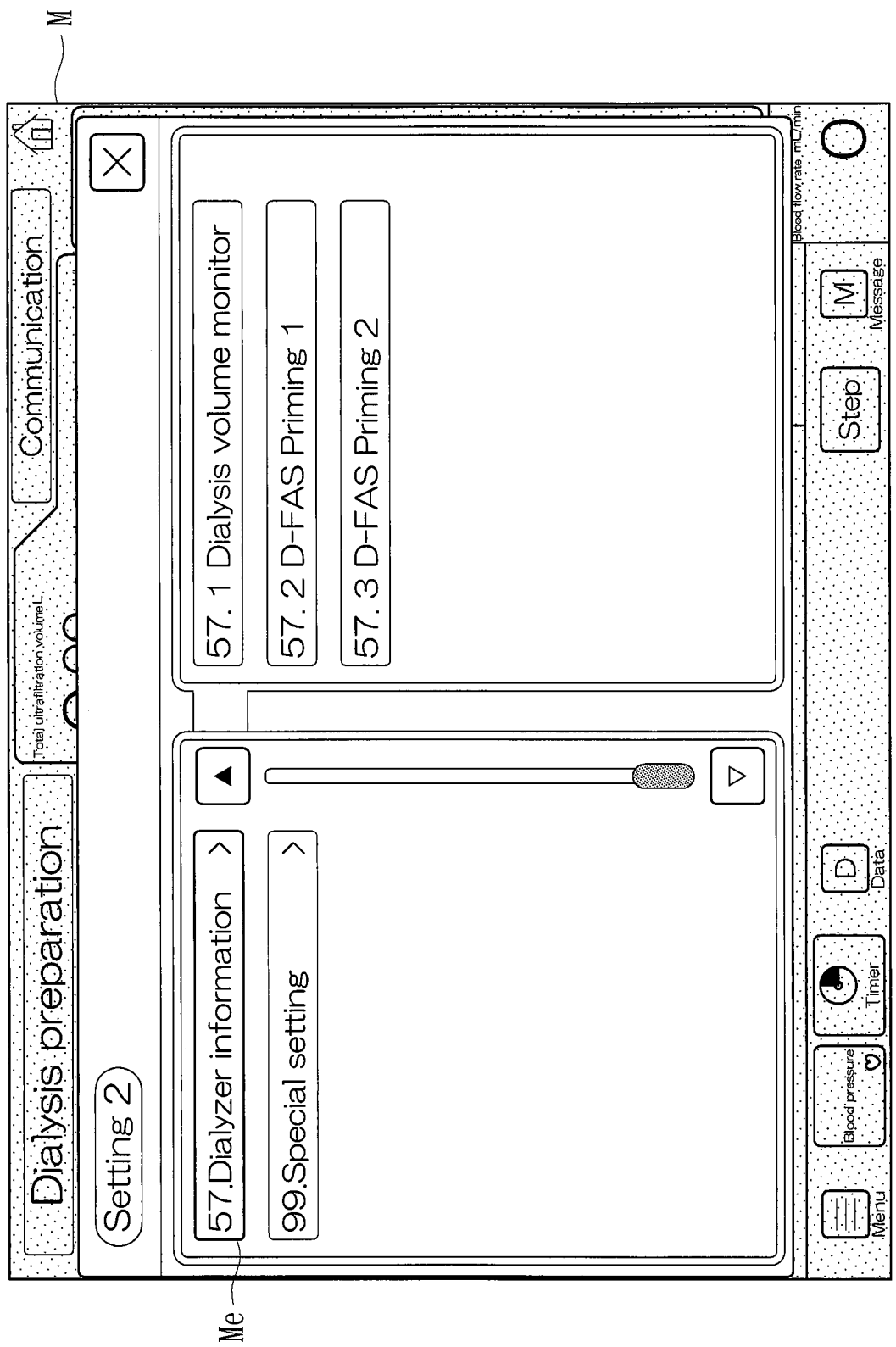
[Fig. 8]

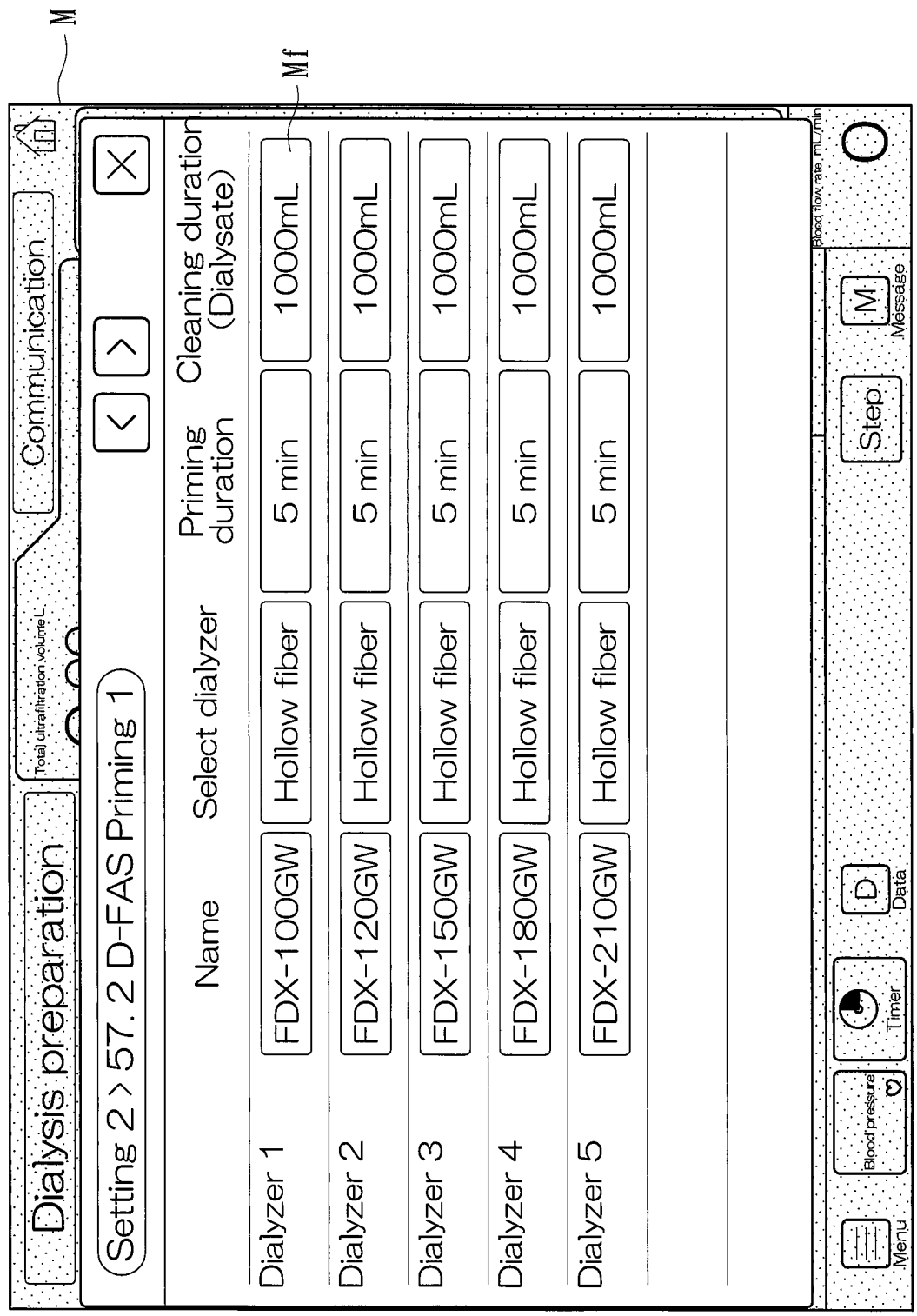
[Fig. 9]

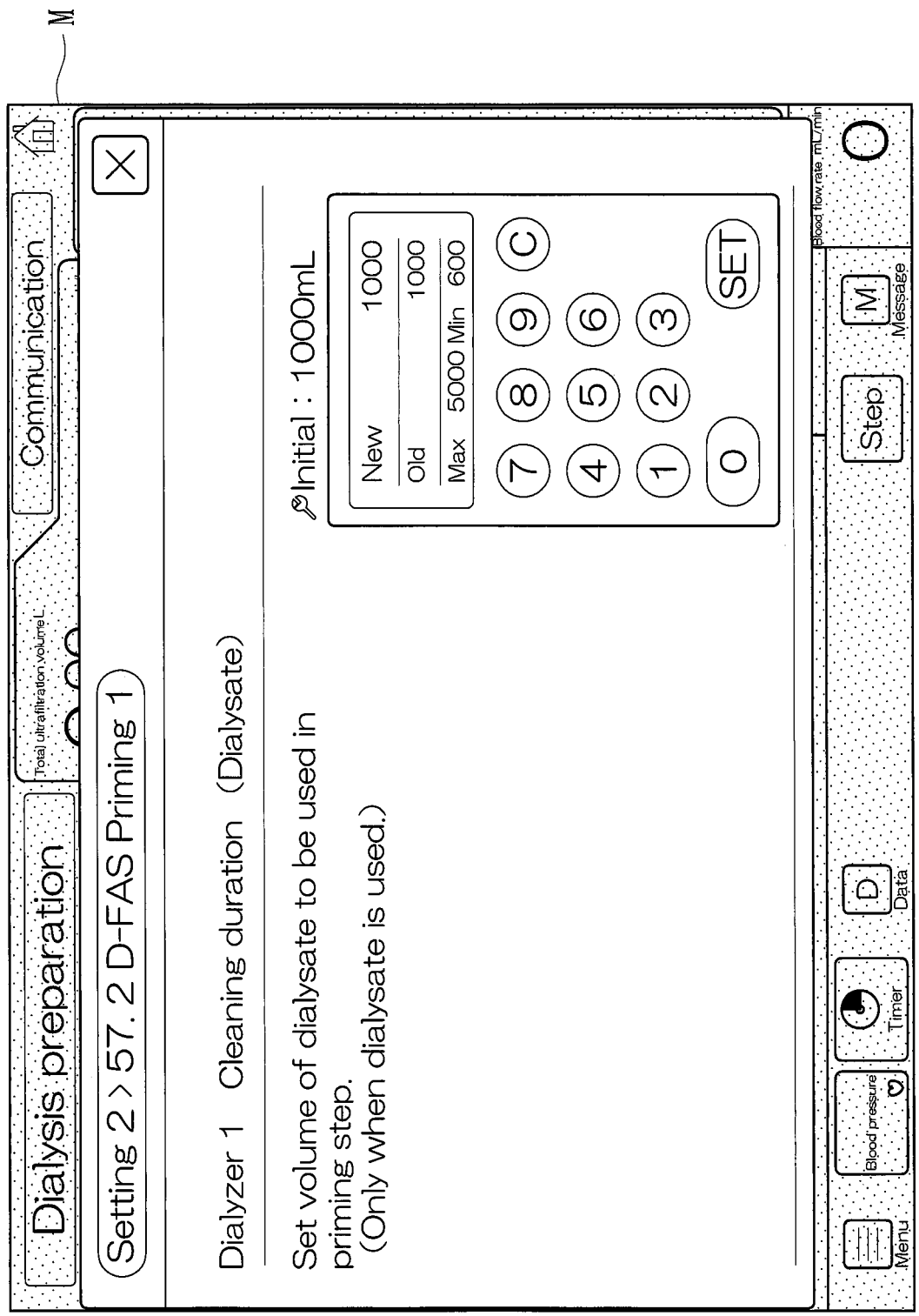
[Fig. 10]

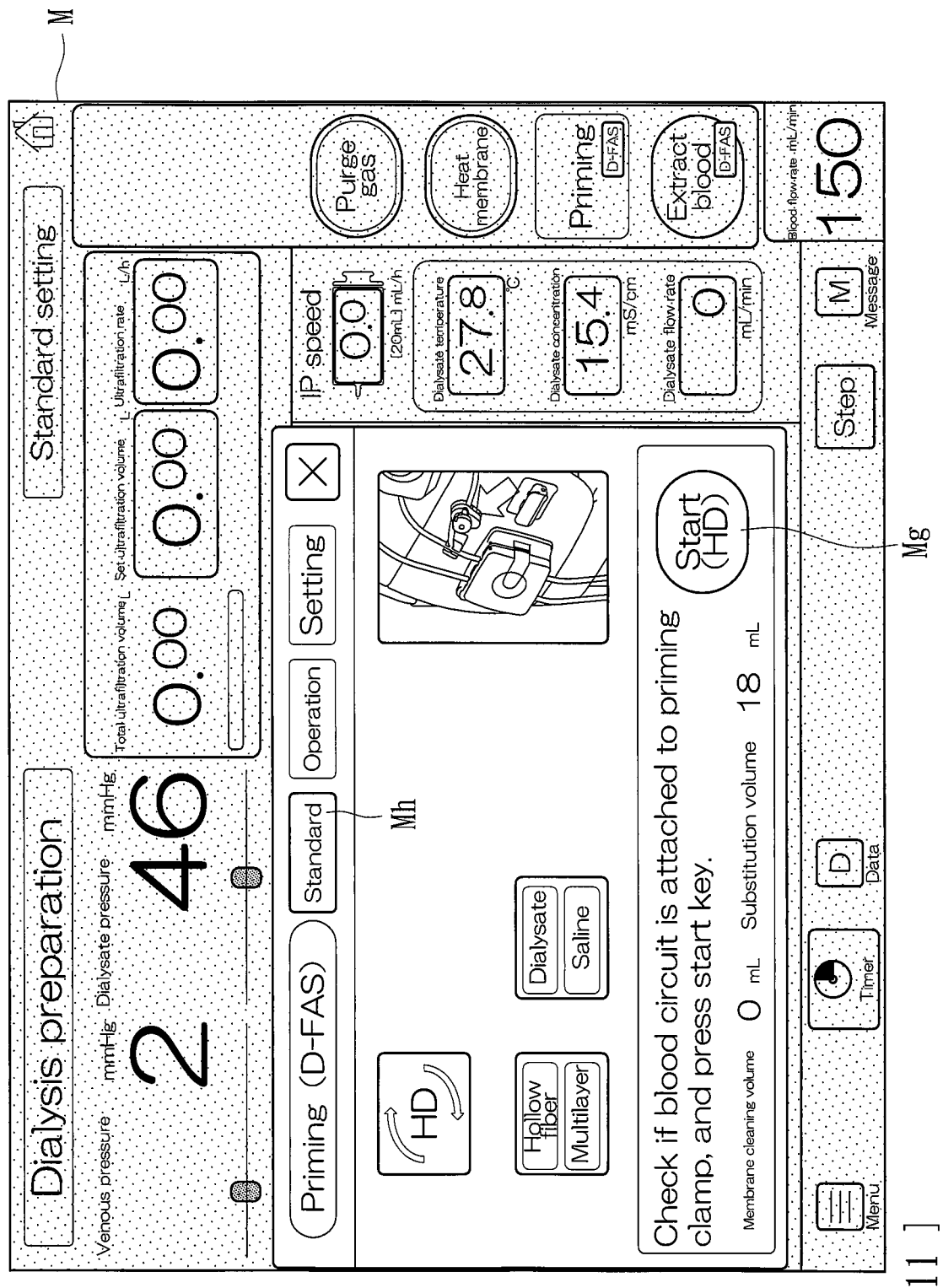
[Fig. 11]

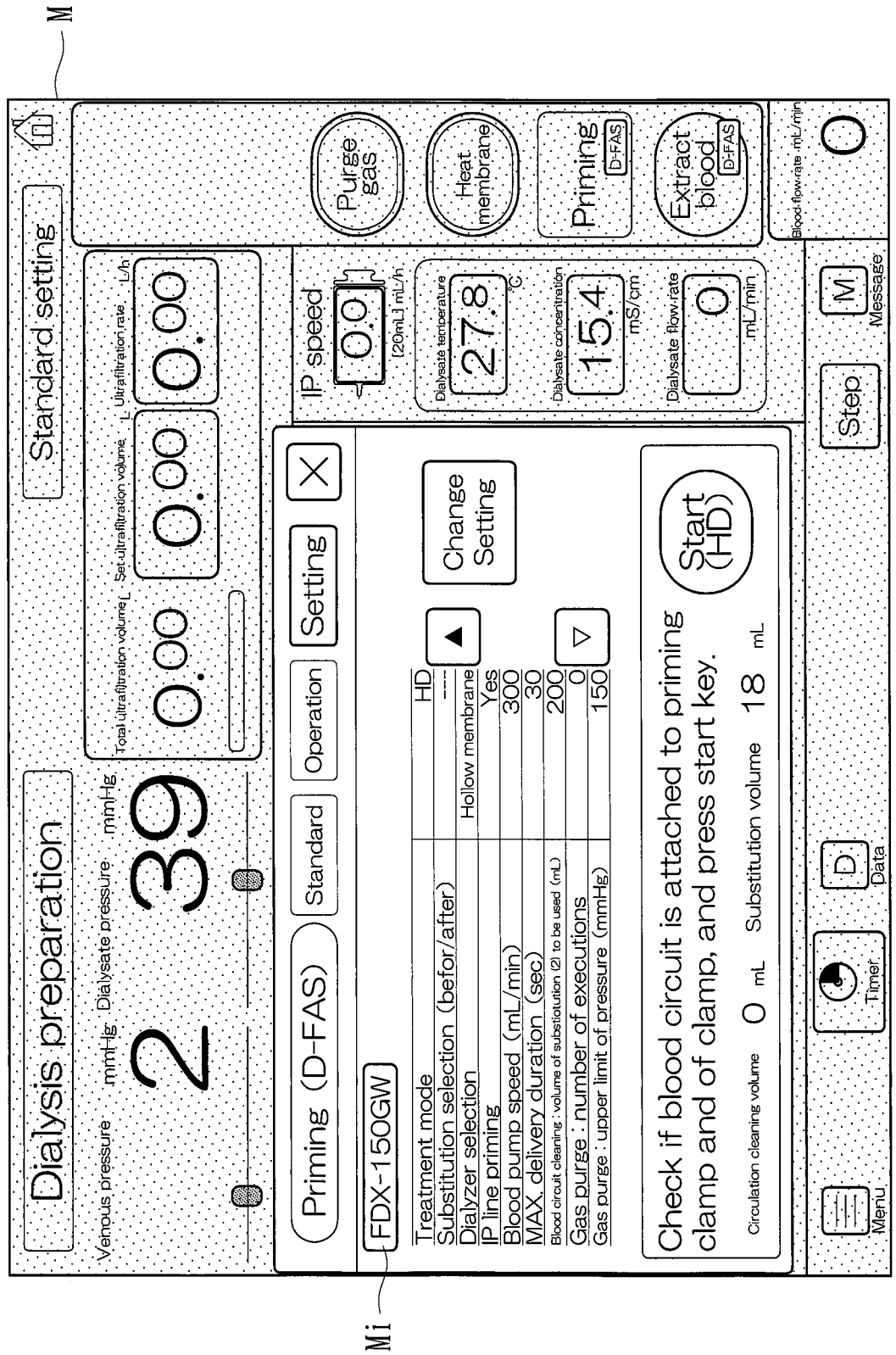
[Fig. 12]

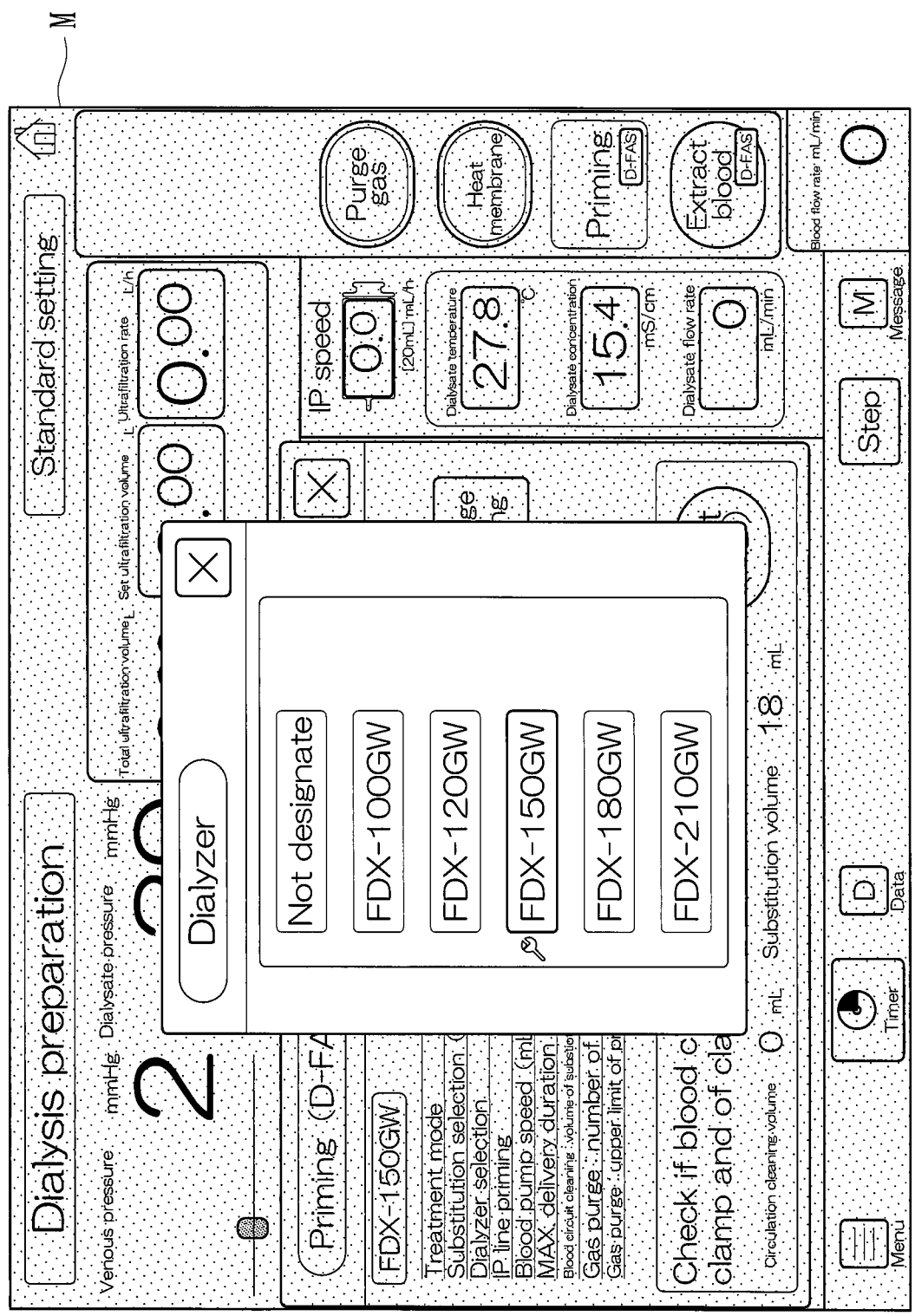
[Fig. 13]

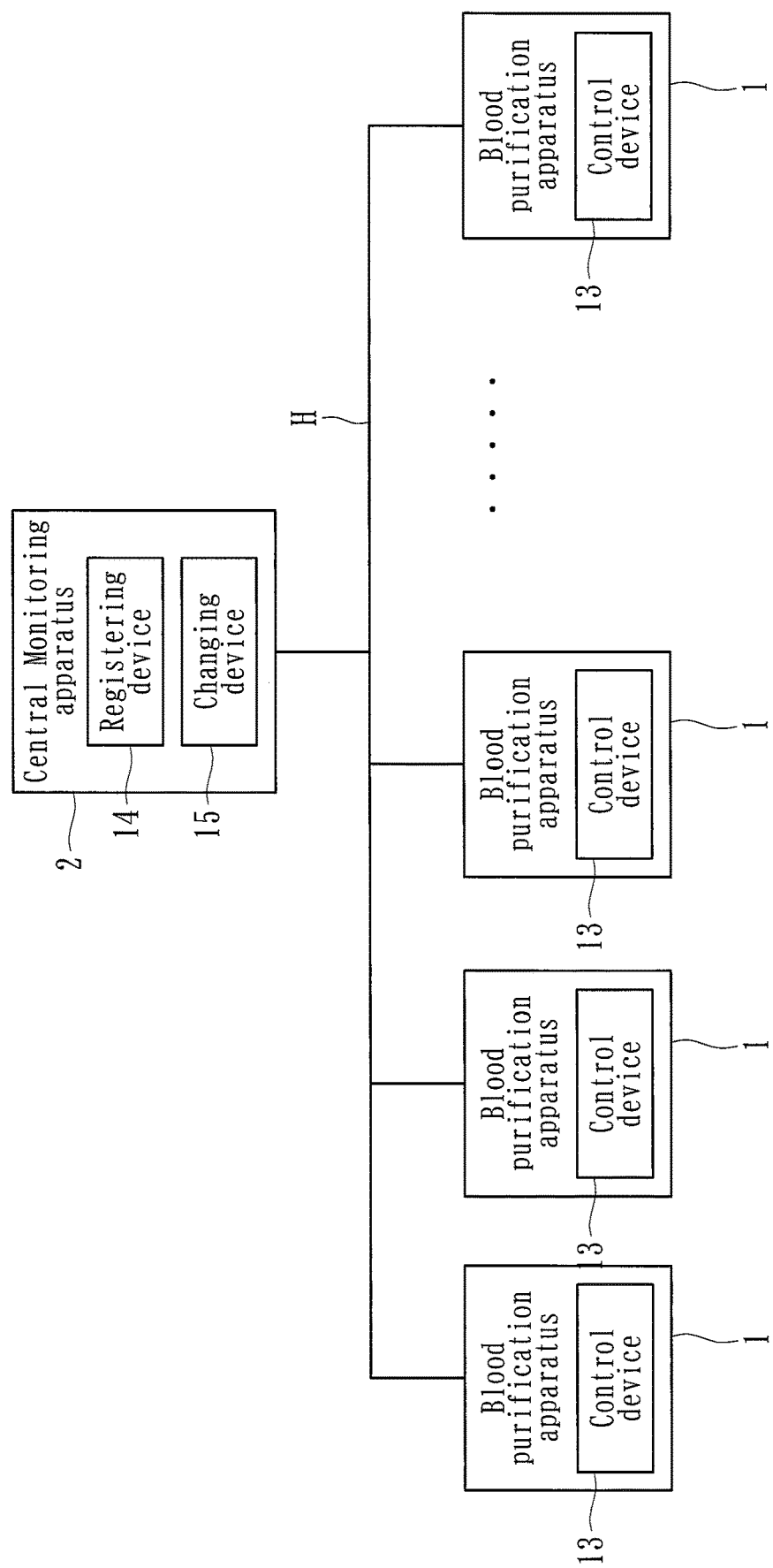
[Fig. 14]

BLOOD PURIFICATION APPARATUS AND BLOOD PURIFICATION SYSTEM

FIELD

The present teaching relates to a blood purification apparatus and a blood purification system for giving blood purification treatment by purifying the blood of a patient.

BACKGROUND

A dialysis room provided in a medical facility such as a hospital is equipped with a plurality of dialysis apparatuses as blood purification apparatuses used in dialysis treatment or the like, so that dialysis treatment (blood purification treatment) is given to many patients in the dialysis room. As disclosed by PTL 1, for example, each of the dialysis apparatuses is connected to a central monitoring apparatus including a server and a terminal and is capable of receiving various pieces of information on the patient that are held by the central monitoring apparatus, so that treatment conditions and operational settings can be determined for each of the patients. An example of a device may be located within PTL 1: Japanese Unexamined Patent Application Publication No. 6-205827 the teachings of which are expressly incorporated by reference herein.

SUMMARY

However, the above known blood purification apparatus has the following problem.

In recent years, there have been cases where the blood purification apparatus includes a blood purifier (in particular, a dialyzer) having an unprecedentedly large capacity. If such a large-capacity blood purifier is used, special treatment conditions and operational settings are required. That is, such settings need to be changed with individuals, which increases the number of steps to be performed by an operator and therefore reduces the ease of operation. This problem occurs not only in a case where the large-capacity blood purifier is used but also in a case where a blood purifier that requires special treatment conditions and operational settings is used.

The present teachings have been conceived in view of the above circumstances and provides a blood purification apparatus and a blood purification system that is operable with increased ease even if a blood purifier that requires special treatment conditions and operational settings is used.

According to the teachings herein, there is provided a blood purification apparatus that includes a blood purifier for giving blood purification treatment by purifying blood of a patient; and a control device that executes, in accordance with preset treatment conditions and/or operational settings, an operation for performing the blood purification treatment or an operation associated with the blood purification treatment. The blood purification apparatus includes a registering device that is capable of registering, in advance, the treatment conditions and/or operational settings corresponding to a performance, characteristic, or function of the blood purifier; and a changing device that is capable of changing the treatment conditions and/or operational settings to the treatment conditions and/or operational settings registered by the registering device, in accordance with the blood purifier to be used in the blood purification treatment.

According to the teachings herein, in the blood purification apparatus herein, the treatment conditions and/or operational settings registered by the registering device include a volume of cleaning or a duration of cleaning in priming or a priming method that corresponds to the blood purifier.

According to the teachings herein, in the blood purification apparatus herein, the registering device registers the treatment conditions and/or operational settings that correspond to a membrane area of the blood purifier to be used in the blood purification treatment.

According to the teaching herein, in the blood purification apparatus herein, the registering device imposes a restriction on or makes a recommendation for the treatment conditions and/or operational settings to be registered, in accordance with the performance, characteristic, or function of the blood purifier.

According to the teachings herein, there is provided a blood purification system including a plurality of blood purification apparatuses each provided with a blood purifier for giving blood purification treatment by purifying blood of a patient; a central monitoring apparatus that is capable of transmitting treatment conditions and/or operational settings to the blood purification apparatuses; and a control device that executes an operation for performing the blood purification treatment or an operation associated with the blood purification treatment, in accordance with the treatment conditions and/or operational settings transmitted from the central monitoring apparatus. The central monitoring apparatus includes a registering device that is capable of registering, in advance, the treatment conditions and/or operational settings corresponding to a performance, characteristic, or function of the blood purifier; and a changing device that is capable of changing the treatment conditions and/or operational settings to the treatment conditions and/or operational settings registered by the registering device, in accordance with the blood purifier to be used in the blood purification treatment.

According to the teachings herein, in the blood purification system taught herein, the treatment conditions and/or operational settings registered by the registering device include a volume of cleaning or a duration of cleaning in priming or a priming method that corresponds to the blood purifier.

According to the teachings herein, in the blood purification system taught herein, the registering device registers the treatment conditions and/or operational settings that correspond to a membrane area of the blood purifier to be used in the blood purification treatment.

According to the teachings herein, in the blood purification system taught herein, the registering device imposes a restriction on or makes a recommendation for the treatment conditions and/or operational settings to be registered, in accordance with the performance, characteristic, or function of the blood purifier.

According to the teachings, the apparatus or the system includes the registering device that is capable of registering, in advance, the treatment conditions and/or operational settings corresponding to the performance, characteristic, or function of the blood purifier; and the changing device that is capable of changing the treatment conditions and/or operational settings to the treatment conditions and/or operational settings registered by the registering device, in accordance with the blood purifier to be used in the blood purification treatment. Therefore, even if a blood purifier that requires special treatment conditions or operational settings is used, the ease of operation can be increased.

According to the teachings herein, the treatment conditions and/or operational settings registered by the registering device include the volume of cleaning or the duration of cleaning in priming or the priming method that corresponds to the blood purifier. Therefore, even if a blood purifier that requires special treatment conditions or operational settings is used, the volume of cleaning or the duration of cleaning in priming or the priming method can be set appropriately.

According to the teachings herein, the registering device registers the treatment conditions and/or operational settings that correspond to the membrane area of the blood purifier to be used in the blood purification treatment. Therefore, even if a blood purifier that requires special treatment conditions or operational settings depending on the membrane area is used, the ease of operation can be increased.

According to the teachings herein, the registering device imposes a restriction on or makes a recommendation for the treatment conditions and/or operational settings to be registered, in accordance with the performance, characteristic, or function of the blood purifier. Therefore, the registering work by the registering device can be made easier, and the occurrence of setting error can be suppressed.

BRIEF DESCRIPTION OF THE DRAWINGS

FIG. 1 is a block diagram of blood purification apparatuses and a central monitoring apparatus according to a first embodiment of the present teaching.

FIG. 2 is a perspective view of an apparatus body of the blood purification apparatus.

FIG. 3 is a schematic diagram of the blood purification apparatus.

FIG. 4 is a schematic view illustrating information provided on a display of the blood purification apparatus.

FIG. 5 is a schematic view illustrating information provided on the display of the blood purification apparatus.

FIG. 6 is a schematic view illustrating information provided on the display of the blood purification apparatus.

FIG. 7 is a schematic view illustrating information provided on the display of the blood purification apparatus.

FIG. 8 is a schematic view illustrating information provided on the display of the blood purification apparatus.

FIG. 9 is a schematic view illustrating information provided on the display of the blood purification apparatus.

FIG. 10 is a schematic view illustrating information provided on the display of the blood purification apparatus.

FIG. 11 is a schematic view illustrating information provided on the display of the blood purification apparatus.

FIG. 12 is a schematic view illustrating information provided on the display of the blood purification apparatus.

FIG. 13 is a schematic view illustrating information provided on the display of the blood purification apparatus.

FIG. 14 is a block diagram of blood purification apparatuses and a central monitoring apparatus according to a second embodiment of the present teaching.

DETAILED DESCRIPTION

Embodiments of the present teaching will now be described specifically with reference to the drawings.

A blood purification apparatus according to a first embodiment is applied to a blood purification system that gives dialysis treatment by purifying patients' blood that is extracorporeally circulated. As illustrated in FIGS. 1 to 3, the blood purification system includes a plurality of blood purification apparatuses 1 each provided with a blood purifier (see FIG. 3) such as a dialyzer 4 for performing blood purification treatment by purifying the blood of a patient, and a central monitoring apparatus 2 connected to each of the blood purification apparatuses 1.

The central monitoring apparatus 2 is connected to the plurality of blood purification apparatuses 1 with LAN cables H, which allow the central monitoring apparatus 2 and each of the blood purification apparatuses 1 to bi-directionally communicate with each other and to transmit and receive information to and from each other. The central monitoring apparatus 2 further includes a server and a terminal (not illustrated) that is a personal computer. Information (patient information, treatment conditions, and/or operational settings) inputted on the terminal can be stored in the server, and the stored information can be transmitted from the server to each of the blood purification apparatuses 1.

The blood purification apparatuses 1 are each a dialysis apparatus for performing dialysis treatment and each include, as illustrated in FIG. 3, a blood circuit 3 including an arterial blood circuit 3a and a venous blood circuit 3b, the dialyzer 4 (a blood purifier) provided between the arterial blood circuit 3a and the venous blood circuit 3b and that purifies the blood flowing in the blood circuit 3, a blood pump 5 provided to the arterial blood circuit 3a and being capable of delivering liquid when activated, an arterial air-trap chamber 6 provided to the arterial blood circuit 3a, a venous air-trap chamber 7 provided to the venous blood circuit 3b, a dialysate introduction line L1 through which dialysate is introduced into the dialyzer 4, a dialysate drain line L2 through which drain liquid is discharged from the dialyzer 4, a control device 13, a registering device 14, and a changing device 15.

As illustrated in FIGS. 2 and 3, the blood purification apparatus 1 includes a dialysis-apparatus body 8, the blood purifier (the dialyzer 4) attached to the dialysis-apparatus body 8, and the blood circuit 3 connected to the blood purifier. The dialysis-apparatus body 8 is also provided with a display M, as well as the blood pump 5. The display M includes a touch panel and is capable of displaying a predetermined information on the blood purification treatment. When a relevant part of the screen is touched, a corresponding input can be made.

The arterial blood circuit 3a is provided with a connector (c) at the distal end thereof, and an arterial puncture needle (a) is connectable to the distal end thereof with the connector (c) interposed therebetween. The arterial blood circuit 3a is also provided with the blood pump 5, which is of a peristaltic type, and the arterial air-trap chamber 6 at respective halfway positions thereof. The venous blood circuit 3b is provided with a connector (d) at the distal end thereof, and a venous puncture needle (b) is connected to the distal end thereof with the connector (d) interposed therebetween. The venous blood circuit 3b is also provided with the venous air-trap chamber 7 at a halfway position thereof.

When the blood pump 5 is activated with the arterial puncture needle (a) at the distal end of the arterial blood circuit 3a and the venous puncture needle (b) at the distal end of the venous blood circuit 3b being stuck in the patient, the blood of the patient flows through the arterial blood circuit 3a while undergoing bubble removal (while bubbles contained therein are removed) in the arterial air-trap chamber 6 and reaches the dialyzer 4, where the blood is purified. Then, the blood flows through the venous blood circuit 3b while undergoing bubble removal (while bubbles contained therein are removed) in the venous air-trap chamber 7 and returns into the body of the patient. Thus, the blood of the patient can be purified by the dialyzer 4 while being extracorporeally circulated through the blood circuit 3 from the distal end of the arterial blood circuit 3a to the distal end of the venous blood circuit 3b.

The venous air-trap chamber 7 is provided with a venous pressure sensor P that is capable of detecting the venous pressure on the basis of the liquid pressure in the venous blood circuit 3b. The venous pressure sensor P is capable of detecting the liquid pressure (the venous pressure) of the blood that is under extracorporeal circulation. Thus, the venous pressure of the blood that is extracorporeally circulated through the blood circuit 3 can be monitored, and any changes in the condition of the patient who is taking the treatment can be found.

The dialyzer 4 has, in a housing thereof, a blood inlet 4a (a blood introduction port), a blood outlet 4b (a blood delivery port), a dialysate inlet 4c (an inlet of the dialysate flow route, or a dialysate introduction port), and a dialysate outlet 4d (an outlet of the dialysate flow route, or a dialysate delivery port). The arterial blood circuit 3a is connected to the blood inlet 4a. The venous blood circuit 3b is connected to the blood outlet 4b. The dialysate inlet 4c and the dialysate outlet 4d are connected to the dialysate introduction line L1 and the dialysate drain line L2, respectively.

The dialyzer 4 houses a plurality of hollow fiber membranes (not illustrated), and such hollow fibers serve as blood purification membranes for purifying the blood. The blood purification membranes in the dialyzer 4 define blood flow routes (each extending between the blood inlet 4a and the blood outlet 4b) in which the blood of the patient flows and dialysate flow routes (each extending between the dialysate inlet 4c and the dialysate outlet 4d) in which the dialysate flows. The hollow fiber membranes serving as the blood purification membranes each have a number of very small holes (pores) extending therethrough from the outer peripheral surface to the inner peripheral surface. Hence, impurities and the like contained in the blood are allowed to penetrate through the membranes into the dialysate.

The arterial blood circuit 3a and the venous blood circuit 3b according to the first embodiment are further provided at the distal portions (near the connectors (c) and (d)) thereof with respective bubble-detecting devices (B1 and B2) capable of detecting gas (bubbles) contained in the blood flowing in the arterial blood circuit 3a and the venous blood circuit 3b during the blood purification treatment. The arterial blood circuit 3a and the venous blood circuit 3b according to the first embodiment are further provided at the distal portions (near the connectors (c) and (d)) thereof with clamping devices Va and Vb capable of opening and closing the respective flow routes when opened and closed.

The dialysate introduction line L1 and the dialysate drain line L2 are provided with a duplex pump 9 that delivers a dialysate prepared to have a predetermined concentration to the dialyzer 4 and discharges waste products and the like (drain liquid) together with the dialysate from the dialyzer 4. Specifically, the duplex pump 9 is provided over the dialysate introduction line L1 and the dialysate drain line L2. When the duplex pump 9 is activated, the dialysate can be introduced into the dialyzer 4 through the dialysate introduction line L1 and the dialysate (the drain liquid) can be discharged from the dialyzer 4 through the dialysate drain line L2.

The dialysate introduction line L1 is provided with electromagnetic valves V1 and V3 and filtration filters F1 and F2. The dialysate to be introduced into the dialyzer 4 can be filtered by the filtration filters F1 and F2, and the flow route of the dialysate is closable or openable at an arbitrary timing by the electromagnetic valves V1 and V3. The dialysate introduction line L1 is connected to the dialysate drain line L2 with bypass lines L4 and L5. The bypass lines L4 and L5 are provided with electromagnetic valves V4 and V5, respectively.

Furthermore, detour lines L3 and L6 for detouring the duplex pump 9 are connected to the dialysate drain line L2. The detour line L6 is provided with an electromagnetic valve V6. The detour line L3 is provided with an ultrafiltration pump 10. Hence, when the ultrafiltration pump 10 is activated in the process of extracorporeally circulating the blood of the patient through the blood circuit 3, ultrafiltration in which water is removed from the blood flowing through the dialyzer 4 can be performed.

Furthermore, the dialysate drain line L2 is provided with a pressurizing pump 11 at a position thereof on the upstream side (the right side in FIG. 3) with respect to the duplex pump 9. The pressurizing pump 11 adjusts the liquid pressure in the dialysate drain line L2 at the duplex pump 9. A detour line L7 extends from a position of the dialysate drain line L2 between the pressurizing pump 11 and the duplex pump 9, with a degassing chamber 12 interposed therebetween. The dialysate drain line L2 and the detour line L7 branching off therefrom are provided with electromagnetic valves V2 and V7, respectively. Hence, the flow route of the dialysate is closable or openable at an arbitrary timing.

The control device 13 is a microcomputer electrically connected to various devices such as actuators and sensors included in the blood purification apparatus 1 and executes an operation for performing blood purification treatment (a blood-purification-treatment step) or operations related to the blood purification treatment (such as a dialysis-preparing step and a blood-returning step) on the basis of predetermined treatment conditions and/or operational settings (in the first embodiment, treatment conditions and/or operational settings transmitted from the central monitoring apparatus 2).

More specifically, the control device 13 is capable of controlling the following exemplary steps sequentially by controlling the various actuators and sensors on the basis of treatment conditions and/or operational settings transmitted from the central monitoring apparatus 2: priming (the dialysis-preparing step) in which the blood circuit 3 and the dialysate flow routes provided in the dialyzer 4 are filled with a priming solution; the blood-purification-treatment step in which the blood of the patient is purified in the dialyzer 4 while the blood is extracorporeally circulated through the blood circuit 3; and the blood-returning step in which the blood in the blood circuit 3 is returned into the patient.

The blood purification apparatus 1 according to the first embodiment includes the registering device 14 and the changing device 15. The registering device 14 is capable of registering, in advance, treatment conditions and/or operational settings corresponding to the performance, characteristics, or function of the blood purifier. In the first embodiment, the registration can be made by making inputs on the display M. For example, the blood purifiers registered by the registering device 14 are classified by the performance based on factors such as the membrane area of the purification membranes and UFR, by the characteristics based on the presence/absence or the amount of a coating agent or the like applied to the purification membranes, and by the function based on the type of the purification membranes such as a hollow-fiber type in which hollow fibers form the purification membranes or a multilayer type. Thus, treatment conditions and/or operational settings corresponding to the performance, characteristics, or function can be registered.

The changing device 15 is capable of changing the treatment conditions and/or operational settings (the treatment conditions and/or operational settings transmitted from the central monitoring apparatus 2) to the treatment conditions and/or operational settings registered by the registering device 14, in accordance with the blood purifier (the dialyzer 4 or the like) to be used in the blood purification treatment. Specifically, when a blood purifier to be used is inputted on the display M, that blood purifier is compared with the blood purifiers registered by the registering device 14. Then, the changing device 15 collectively and automatically changes the treatment conditions and/or the operational settings to those set forth for a corresponding one of the blood purifiers registered by the registering device 14.

Examples of the treatment conditions and/or operational settings that are registered by the registering device 14 include the following. For the dialysis-preparing step, the volume of cleaning or the duration of cleaning in priming or the priming method can be named. For the blood-purification-treatment step, the volume of anticoagulant to be used (the rate of infusion, the volume of infusion, or the like of the anticoagulant), the monitoring of warnings (such as the monitoring of warning points of pressures such as the venous pressure, the inlet pressure of the dialyzer 4, the dialysate pressure, and TMP (transmembrane pressure difference); and the reduction in UFR), the blood flow rate (the driving speed of the blood pump 5), the clearance of the dialyzer 4 that is detected by a dialysis-volume monitor, or the like can be named. Other treatment conditions and/or operational settings registered by the registering device 14 include the volume of blood returned in the blood-returning step (the volume of blood to be returned after the blood purification treatment, which is determined by the speed of rotation of the blood pump or the like).

In particular, the registering device 14 according to the first embodiment registers treatment conditions and/or operational settings corresponding to the membrane area of the blood purifier (the dialyzer 4 or the like) to be used in the blood purification treatment. Specifically, in a large-capacity blood purifier, the volume of cleaning in the priming tends to be greater and the duration of cleaning in priming therefore tends to be longer than in a normal blood purifier. Hence, parameters for an increased volume of cleaning and an increased duration of cleaning in priming are registered.

If a blood purifier whose purification membranes such as hollow fiber membranes are coated with a coating agent (such as glycerin for protecting the purification membranes, or PVP as a hydrophilizing agent), parameters for an increased volume of cleaning and an increased duration of cleaning in priming are registered so that the coating agent does not remain when the blood purifier is used. Furthermore, a large-capacity blood purifier tends to require an increased volume of anticoagulant. Therefore, treatment conditions and/or operational settings to be registered include parameters for a volume of anticoagulant to be used that is greater than usual.

Here, the term UFR refers to the rate of water removal in ultrafiltration and is a numerical parameter indicating how much water is allowed to permeate in accordance with time and pressure. Thus, the water permeability of the dialyzer 4 can be expressed. The higher the UFR, the higher the water permeability. To detect any clogging in the purification membranes (hollow fiber membranes) of the dialyzer 4, the blood purification apparatus (the dialysis apparatus) employs a monitoring method (UFR monitoring) in which the UFR immediately after the start of the treatment is measured and a predetermined level of reduction in the UFR from the measured UFR is detected. In most cases, a large-capacity blood purifier (a dialyzer 4 or the like having a large membrane area) is used for a patient who needs an increased removal effect, and such a blood purifier therefore has a high UFR. In the case where a large-capacity blood purifier having a high UFR is used, if UFR is measured immediately after the start of the treatment so that UFR monitoring is performed, the UFR may be too high to measure. Therefore, if a large-capacity blood purifier is used, treatment conditions and/or operational settings are changed to those registered by the registering device 14 to change the monitoring method to another suitable monitoring method instead of UFR monitoring.

Furthermore, the registering device 14 according to the first embodiment is configured to impose restrictions on or make recommendations for the treatment conditions and/or operational settings to be registered, in accordance with the performance, characteristics, or function of the blood purifier. Specifically, the blood purifier and the treatment conditions and/or operational settings corresponding to the blood purifier that are registered by the registering device 14 are preferably based on parameters suitable for the performance, characteristics, or function of that blood purifier. Therefore, for example, when registration is made on the display M, recommended treatment conditions and/or operational settings are displayed so that they are selectively registered, or some treatment conditions and/or operational settings are restricted such that they cannot be inputted.

Now, a method of registering and setting a blood purifier according to the first embodiment will be described.

First, as illustrated in FIG. 4, various pieces of information regarding the preparation for blood purification treatment are displayed in the initial screen on the display M, as well as operation buttons Ma and Mb for making inputs. When an operator touches the operation button Mb ("MENU") so as to make registration through the registering device 14, a subscreen illustrated in FIG. 5 appears. When the operator touches an operation button Mc ("SETTING") provided in the subscreen, another subscreen appears as illustrated in FIG. 6. When the operator touches an operation button Md ("SETTING 2") provided in the subscreen, a window for making selection illustrated in FIG. 7 appears.

In the selection window, when an operation button Me denoting "dialyzer information" (see FIG. 8) is touched, a registration window appears as illustrated in FIG. 9. In the registration window, items including information that identifies blood purifiers (product names or the like), the type thereof (the hollow-fiber-membrane type, the multilayer type, or the like), and treatment conditions and/or operational conditions (in the first embodiment, priming duration and cleaning duration) are displayed. When one of predetermined items (for example, a predetermined item Mf) is touched, an input window illustrated in FIG. 10 through which an input can be made appears.

In the input window, the parameter regarding the predetermined item Mf can be changed. If a blood purifier named "Dialyzer 1" is used, the volume of cleaning solution (the volume of dialysate) to be used in the priming step can be set. That is, a set of treatment conditions and/or operational conditions can be registered in association with the blood purifier registered as "Dialyzer 1". Of course, if any other predetermined item listed as "Name" in the window illustrated in FIG. 9 is touched, a corresponding one of the blood purifiers can be registered.

Before the blood purification treatment is performed and while the initial screen illustrated in FIG. 4 is displayed, the blood purifier (the dialyzer 4 or the like) and the blood circuit 3 are attached to the dialysis-apparatus body 8. Subsequently, when the operation button Ma ("PRIMING"), for example, is touched and an input is made, another subscreen appears as illustrated in FIG. 11. If it is not intended to select the blood purifier to be used, touch and input an input button Mg ("START(HD)") in the subscreen. Thus, priming is started on the basis of preset treatment conditions and/or operational settings (the treatment conditions and/or operational settings transmitted from the central monitoring apparatus 2).

In the subscreen illustrated in FIG. 11, when an operation button Mh ("STANDARD") is touched, yet another subscreen appears as illustrated in FIG. 12. When an operation button Mi provided in the subscreen is touched, a small window for making selection appears as illustrated in FIG. 13. In this window, a plurality of names (product names or the like) of the blood purifiers registered in advance by the registering device 14 are displayed. When a blood purifier desired to be used is touched, the changing device 15 changes the settings to corresponding ones of the treatment conditions and/or operational conditions registered by the registering device 14. In this case, the dialyzer named "FDX-150GW" is selected as the blood purifier to be used. Then, on condition that the input button Mg provided in the screen illustrated in FIG. 11 has been touched, priming is performed with the treatment conditions and/or operational settings corresponding to the selected blood purifier.

The first embodiment employs the registering device 14 that is capable of registering, in advance, treatment conditions and/or operational settings corresponding to the performance, characteristics, or function of the blood purifier; and the changing device 15 that is capable of changing, in accordance with the blood purifier (the dialyzer 4 or the like) to be used in the blood purification treatment, the treatment conditions and/or operational settings to the treatment conditions and/or operational settings registered by the registering device 14. Therefore, even if a blood purifier that requires special treatment conditions or operational settings is used, the ease of operation can be increased.

Furthermore, the treatment conditions and/or operational settings that are registered by the registering device 14 include the volume of cleaning or the duration of cleaning in priming or the priming method that corresponds to the blood purifier. Therefore, even if a blood purifier that requires special treatment conditions or operational settings is used, the volume of cleaning or the duration of cleaning in priming or the priming method can be set appropriately. Furthermore, the registering device 14 registers treatment conditions and/or operational settings corresponding to the membrane area of the blood purifier to be used in the blood purification treatment. Therefore, even if a blood purifier that requires special treatment conditions or operational settings depending on the membrane area is used, the ease of operation can be increased. Furthermore, the registering device 14 imposes restrictions on or makes recommendations for the treatment conditions and/or operational settings to be registered, in accordance with the performance, characteristics, or function of the blood purifier. Therefore, the registering work by the registering device 14 can be made easier, and the occurrence of setting error can be suppressed.

Now, a second embodiment of the present teaching will be described.

As with the first embodiment, a blood purification apparatus according to the second embodiment is applied to a blood purification system that gives dialysis treatment by purifying patients' blood that is extracorporeally circulated. As illustrated in FIG. 14, the blood purification system includes a plurality of blood purification apparatuses 1 each provided with a blood purifier (see FIG. 3) such as a dialyzer 4 for performing blood purification treatment by purifying the blood of a patient, and a central monitoring apparatus 2 connected to each of the blood purification apparatuses 1. Elements that are the same as those described in the first embodiment are denoted by corresponding ones of the reference numerals, and detailed description of those elements is omitted. In the blood purification system according to the second embodiment, the central monitoring apparatus 2 includes the registering device 14 that is capable of registering, in advance, treatment conditions and/or operational settings corresponding to the performance, characteristics, or function of the blood purifier; and the changing device 15 that is capable of changing the treatment conditions and/or operational settings to the treatment conditions and/or operational settings registered by the registering device 14, in accordance with the blood purifier to be used in the blood purification treatment. Therefore, the registration through the registering device 14 and the setting of items such as treatment conditions and/or operational settings can be performed on the central monitoring apparatus 2. Accordingly, there is no need to perform those operations on each of the blood purification apparatuses 1.

While some embodiments have been described above, the present teaching is not limited thereto. For example, the present teaching may be applied to a dialysis apparatus that is not connected to the central monitoring apparatus 2. In that case, treatment conditions and/or operational settings are set on the blood purification apparatus in advance, and the treatment conditions and/or operational settings corresponding to the performance, characteristics, or function of the blood purifier are registered. Then, in accordance with the blood purifier to be used, the preset treatment conditions and/or operational settings are changed, and the control device 13 performs a relevant control operation (a control operation that executes an operation for giving blood purification treatment or an operation associated with the blood purification treatment).

In addition, the blood purification apparatuses 1 may be connected to the central monitoring apparatus 2 without using cables such as the LAN cables H (for example, the blood purification apparatuses 1 and the central monitoring apparatus 2 may be incapable of bi-directional communication, or may be capable of radio communication). Moreover, while the above embodiments are each applied to a hemodialysis apparatus that is capable of performing a treatment method such as hemodialysis (HD), ECUM, or HDF (hemodiafiltration), the present teaching may be applied to a blood purification apparatus that is capable of giving any other blood purification treatment (such as hemofiltration (HF) or continuous hemofiltration (CHF)).

The present teaching is applicable to any blood purification apparatus and any blood purification system each having a different appearance, any additional functions, or the like, as long as the apparatus or the system includes a registering device that is capable of registering, in advance, treatment conditions and/or operational settings corresponding to the performance, characteristics, or function of the blood purifier; and a changing device that is capable of changing the treatment conditions and/or operational settings to the treatment conditions and/or operational settings registered by the registering device, in accordance with the blood purifier to be used in the blood purification treatment.

REFERENCE SIGN LIST 1 blood purification apparatus
2 central monitoring apparatus 3 blood circuit
4 dialyzer (blood purifier)
5 blood pump
6 arterial air-trap chamber
7 venous air-trap chamber
8 apparatus body
9 duplex pump
10 ultrafiltration pump
11 pressurizing pump
12 degassing chamber
13 control device
14 registering device
15 changing device

We claim:

1. A blood purification apparatus that includes:
a blood purifier for giving blood purification treatment by purifying blood of a patient; and
a control device that executes, in accordance with preset treatment conditions and/or operational settings, an operation for performing the blood purification treatment or an operation associated with the blood purification treatment,
the blood purification apparatus comprising:
a registering device that registers, in advance, the treatment conditions and/or operational settings corresponding to a performance, characteristic, or function of a plurality of blood purifiers; and
a changing device that changes the treatment conditions and/or operational settings to the treatment conditions and/or operational settings registered by the registering device, in accordance with the blood purifier to be used, in the blood purification treatment;
wherein the registering device imposes a restriction on or makes a recommendation for the treatment conditions and/or operational settings to be registered, in accordance with the performance, characteristic, or function of the blood purifier; and
wherein when the blood purifier to be used from the plurality of blood purifiers is input, the changing device changes the treatment conditions and/or operational settings to those corresponding to the blood purifier to be input from the plurality of blood purifiers registered by the registering device.

2. The blood purification apparatus according to claim 1, wherein the treatment conditions and/or operational settings registered by the registering device include a volume of cleaning or a duration of cleaning in priming or a priming method that corresponds to each of the plurality of blood purifiers.

3. The blood purification apparatus according to claim 1, wherein the registering device registers the treatment conditions and/or operational settings that correspond to a membrane area of the blood purifier to be used in the blood purification treatment.

4. A blood purification system comprising:
a plurality of blood purification apparatuses each provided with a blood purifier for giving blood purification treatment by purifying blood of a patient;
a central monitoring apparatus that is capable of transmitting treatment conditions and/or operational settings to the blood purification apparatuses; and
a control device that executes an operation for performing the blood purification treatment or an operation associated with the blood purification treatment, in accordance with the treatment conditions and/or operational settings transmitted from the central monitoring apparatus,
wherein the central monitoring apparatus includes:
a registering device that registers, in advance, the treatment conditions and/or operational settings corresponding to a performance, characteristic, or function of a plurality of blood purifiers; and
a changing device that changes the treatment conditions and/or operational settings to the treatment conditions and/or operational settings registered by the registering device, in accordance with the blood purifier to be used in the blood purification treatment;
wherein the registering device imposes a restriction on or makes a recommendation for the treatment conditions and/or operational settings to be registered, in accordance with the performance, characteristic, or function of the blood purifier selected from the plurality of blood purifiers; and
wherein when the blood purifier to be used is input from the plurality of blood purifiers, the changing device changes the treatment conditions and/or operational settings to those corresponding to the blood purifier to be input from the plurality of blood purifiers registered by the registering device.

5. The blood purification system according to claim 4, wherein the treatment conditions and/or operational settings registered by the registering device include a volume of cleaning or a duration of cleaning in priming or a priming method that corresponds to each of the plurality of blood purifiers.

6. The blood purification system according to claim 4, wherein the registering device registers the treatment conditions and/or operational settings that correspond to a membrane area of the blood purifier to be used in the blood purification treatment.

7. The blood purification apparatus according to claim 1, wherein the control device provides user instructions to carry out one or more operations prior to beginning blood purification treatment.

8. The blood purification system according to claim 4, wherein the control device provides user instructions to carry out one or more operations prior to beginning blood purification treatment.

9. The blood purification apparatus according to claim 1, further comprising a measurement device that measures a rate of water permeability (UFR) through a membrane of the blood purification apparatus immediately after starting the blood purification treatment.

10. The blood purification system according to claim 4, further comprising a measurement device that measures a rate of water permeability (UFR) through a membrane of the blood purification apparatus immediately after starting the blood purification treatment.

11. The blood purification apparatus according to claim 9, further comprising a detecting device that detects a predetermined level of reduction in the UFR from the measured UFR.

12. The blood purification system according to claim 10, further comprising a detecting device that detects a predetermined level of reduction in the UFR from the measured UFR.

13. A central monitoring apparatus comprising the blood purification apparatus of claim 1.

14. The central monitoring apparatus of claim 13, wherein the central monitoring apparatus is connected to a plurality of the blood purification apparatuses and the central monitoring apparatus and the plurality of blood purification apparatus bi-directionally communicate to transmit and receive information.

15. The blood purification apparatus of claim 1, wherein the control device primes a blood circuit and dialysate flow routes with a priming solution.

16. The blood purification apparatus of claim 1, wherein a type of blood purifier to be used in the blood purification is registered by the registering device and the changing device automatically changes the treatment conditions and/or the operational settings to settings corresponding to one of a blood purifier registered by the registering device.

17. The blood purification apparatus of claim 16, wherein the treatment conditions and/or the operational settings include a volume of cleaning, a duration of cleaning, a priming method, a volume of anticoagulant, a dialysate pressure, a volume of blood returned in a blood-return step, or a combination thereof.

18. The blood purification system of claim 4, wherein the registering device displays the recommendation for the treatment conditions and/or the operational setting to restrict treatment conditions and/or operational settings that can be inputted.

19. The blood purification system of claim 4, wherein registration through the registration device occurs through a central monitoring apparatus.

20. The blood purification system of claim 4, wherein the registering device displays the plurality of blood purifiers that are registered and once a desired one of the plurality of blood purifiers is selected the changing device changes settings corresponding to the desired one of the plurality of blood purifiers.

* * * * *